(12) United States Patent
Lohr (10) Patent No.: US 7,329,793 B1
(45) Date of Patent: Feb. 12, 2008

(54) EXTRAVASCULAR ROLLER DEVICE AND METHOD OF REMOVING SUBCUTANEOUS FLUID

(76) Inventor: Charles E. Lohr, 990 Irwin St., Apt. 9B, Morgantown, WV (US) 26505

( * ) Notice: Subject to any disclaimer, the term of this patent is extended or adjusted under 35 U.S.C. 154(b) by 433 days.

(21) Appl. No.: 10/794,197

(22) Filed: Mar. 5, 2004

Related U.S. Application Data (60) Provisional application No. 60/452,438, filed on Mar. 6, 2003.

(51) Int. Cl.
*A61F 13/20* (2006.01)
(52) U.S. Cl. ............... 604/362; 604/366; 604/368; 604/370; 604/319
(58) Field of Classification Search ............... 604/362, 604/366, 368, 370, 319; 602/213, 215; 601/122, 601/123, 119
See application file for complete search history.

(56) References Cited

U.S. PATENT DOCUMENTS

| | | | | |
|---|---|---|---|---|
| 3,739,771 A | * | 6/1973 | Gaquer et al. ............... 601/97 |
| 4,753,478 A | * | 6/1988 | Weinreich ............... 297/284.5 |
| 6,068,605 A | * | 5/2000 | Bjørnsti ............... 601/119 |
| 6,190,338 B1 | * | 2/2001 | Arndt ............... 601/115 |
| 2002/0099409 A1 | * | 7/2002 | Hui ............... 606/201 |
| 2005/0159688 A1 | * | 7/2005 | Sakamoto et al. ............... 601/123 |

* cited by examiner

*Primary Examiner*—Jacqueline F. Stephens
(74) *Attorney, Agent, or Firm*—Johnston Holroyd; Mary-Jacq Holroyd (57) ABSTRACT

A roller device has a handle with two arms extending from one end of a handgrip and a roller which is cylindrical having a surface composed of a spongy material, and two ends having an opening through the center of each end. The arms have ends which rotatably engage one opposing opening of the roller. The roller may have an inner part and an outer part with a spongy material on the surface of the outer part, or the entire outer part may be a spongy material. A method of using the roller device involves placing the roller on a leg above a top incision, rolling the device down the leg while applying moderate pressure, forcing fluids down and out a lower incision, wiping off the fluid, observing for additional fluid build up, and repeating the procedure until no further build up is observed.

12 Claims, 6 Drawing Sheets

EXTRAVASCULAR ROLLER DEVICE AND METHOD OF REMOVING SUBCUTANEOUS FLUID

RELATED APPLICATIONS

This application claims the benefit of U.S. Provisional Application Ser. No. 60/452,438 filed on Mar. 6, 2003, the contents of which are incorporated herein in their entirety.

FIELD OF THE INVENTION

The present invention relates to a medical device, and more particularly to an extravascular roller device used to remove blood and other fluids generated upon the endoscopic removal of a saphenous vein from a leg during coronary bypass grafting.

BACKGROUND OF THE INVENTION

Coronary bypass is the surgical treatment for coronary heart disease, and is used to relieve angina pectoris and prevent myocardial infarction. One or more blood vessels, usually an artery in the chest or a vein from the leg, are transplanted (grafted) to create new paths for blood to flow from the aorta to the heart muscle, bypassing obstructed sections of the coronary arteries. Saphenous veins are commonly used as bypass conduits in coronary bypass grafting.

Saphenous veins are either of two chief superficial veins of the leg. The vein, which originates in the foot and passes up the medial side of the leg and through the saphenous opening to join the femoral vein, is called either the internal saphenous vein or the long saphenous vein. The other vein originates similarly and passes up the back of the leg to join the popliteal at the knee, which is called either the external saphenous vein or the short saphenous vein. These veins are harvested from the leg and attached to the heart's circulatory system to bypass arteries that are not providing sufficient blood flow.

Aortacoronary bypass surgery means that one or more bypass grafts are implanted between the aorta and the coronary blood vessel. If occlusive vascular disease limits the blood flow to the heart, the bypass graft bridges the occluded, or diseased, heart blood vessel (coronary artery), and brings new blood to the heart. Saphenous veins (from the leg) or arteries (like the internal mammary artery) are commonly used as grafts for coronary bypass surgery. All bypasses were originally performed using the saphenous vein from the leg to carry blood around the obstruction. The vein was attached at one end to the aorta and at the other end to the coronary artery distal to the blockage or occlusion could be considered.

The procedure for harvesting the veins involves an incision made close to the knee to identify the saphenous vein and introduce the endoscope. Additional small "stab" incisions may be made at the ankle or at the groin to retrieve the harvested vein. A fiber optic endoscope is introduced through the incision at the knee to allow the doctor to view and harvest the vein from the inner thigh and/or calf, depending on the surgeon's preference for the vein conduit. Exploration of either area is accomplished by blunt dissection aided by $CO_2$ insluffation. Branches of the saphenous vein are divided by cautery. The vein is then removed through the tiny incisions at the ankle or groin.

This vein on the inside of the leg running from the ankle to the groin can be used to make bypasses from the aorta to the coronary arteries. There is a deep venous system that normally does most of the work draining blood from the legs back to the heart. The saphenous vein is part of the superficial system that normally does only about 10% of the work. The saphenous vein can, therefore, be taken out without harming the patient or adversely affecting the leg. An endoscopic instrument is introduced through these upper incisions to allow the doctor to view the inside of the inner calf. Instruments are then introduced through the incisions that explore the area, close off the ends of the veins that will remain in the leg, and cut the vein. The vein is then removed through small incisions at the ankle or at the knee. The incisions described are then closed, typically using conventional sutures, and the leg is cleaned.

It is common for the leg from which the vein is harvested to swell slightly. Trauma to the leg during this part of the procedure causes blood to ooze from the subcutaneous tissue. Accumulation of blood in the leg wound tunnels during coronary artery bypass is exacerbated by the requirement for anticoagulation. The blood is removed from inside the leg to avoid blood collection, possible infection and pain. Furthermore, it is desirable to remove the fluids to facilitate healing.

Blood is currently removed from the leg by having the surgeon or surgical assistant roll up a piece of gauze, place the gauze on the calf, and roll it down the leg manually while applying pressure so that the blood will drain from the lower incision site. This procedure is repeated during the surgery until the completion of surgery.

None of the above inventions, taken either singularly or in combination, is seen to describe the instant invention as claimed.

SUMMARY OF THE INVENTION

The present invention relates to an extravascular roller device and a method of using the roller device to remove blood and fluids which pool in the leg following the removal of a saphenous vein during coronary bypass grafting procedures. The roller device of the present invention has a handle made of an autoclavable, rigid material, such as stainless steel. The roller device has two arms extending from one end of the handle. The handle portion of the instrument and the two arms are preferably made of an autoclavable, rigid material, such as stainless steel. The handle of the instrument may be sterilized after each surgery and then reused.

A roller is rotatably engaged on the arms opposite the handle. The roller has a foam outer surface that is flexible and can conform to the various sizes and contours of a patient's calves. An inner part of the roller may be made up of a rigid substance, such as plastic, and when present, is attached to the end of the arms of the handle. The inner part of the roller is sufficiently rigid to withstand the pressure from the user's hand as the roller is repeatedly rolled extracorporeal from the top incision to the bottom incision, see FIG. 1. The roller is detachable and can be replaced after each surgery. Alternatively, the outer foam layer may be replaced for each surgery and the inner part may be autoclaved. The two arms are provided so that pressure is evenly distributed on the patient's leg.

An aspect of the present invention is to provide an instrument that can be used to remove blood from the leg during coronary bypass surgery. The present invention eliminates the need to roll gauze down the leg by hand.

Another aspect of the present invention is that the endoscopic roller device is a simpler, faster and more effective means to accomplish the same purpose.

Yet another aspect of the present invention is to provide a sterilized instrument that can be used to remove blood from the leg during coronary bypass surgery.

A further aspect of the present invention is to provide an instrument which has a spongy surface capable of conforming to the surface of the leg thereby assuring more even application of pressure to the outer surface of the leg.

These and other aspects of the present invention will become readily apparent upon further review of the following drawings and specification.

BRIEF DESCRIPTION OF THE DRAWINGS

The novel features of the described embodiments are specifically set forth in the appended claims; however, embodiments relating to the structure and process of making the present invention, may best be understood with reference to the following description and accompanying drawings.

FIG. 4b is a side view of a roller handle which may be used with the roller of FIG. 4a.

Similar reference characters denote corresponding features consistently throughout the attached drawings.

DETAILED DESCRIPTION OF PREFERRED EMBODIMENTS

Figure 2:
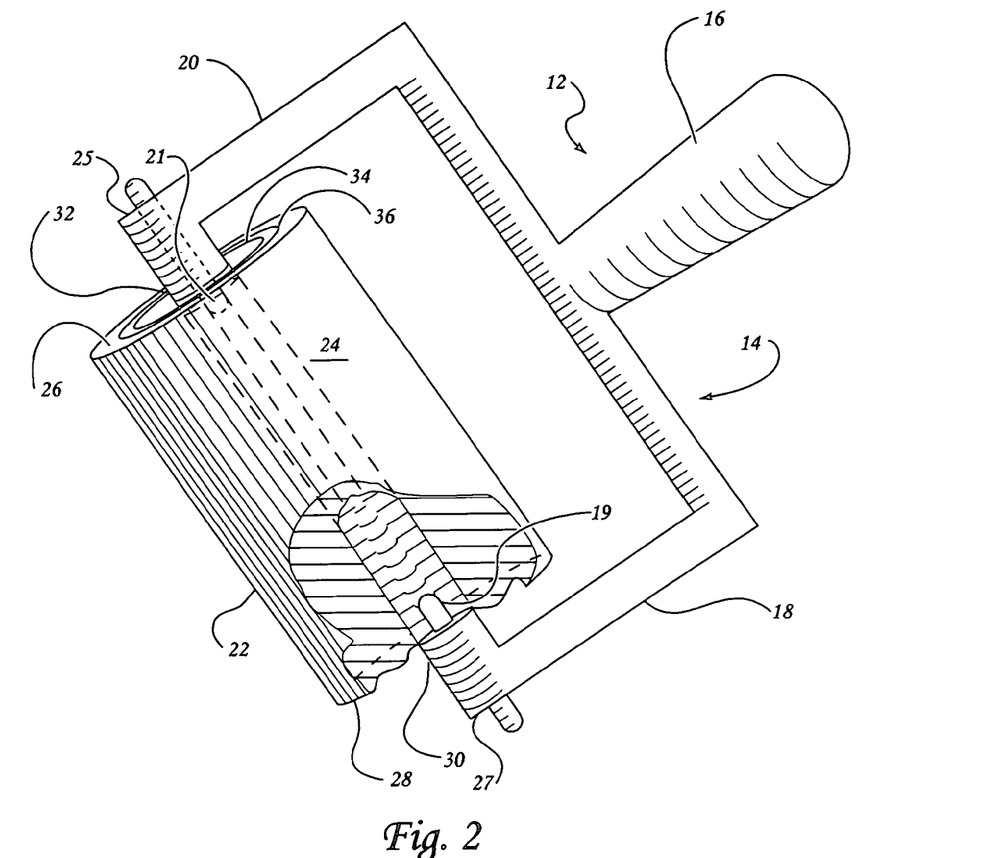
FIG. 2 is a side view of an embodiment of an extravascular roller and handle of the present invention.

An embodiment of the extravascular roller device 12 of the present invention is shown in FIG. 2. The extravascular roller device 12 has a handle 14 and a roller 22. The handle 14 is made of an autoclavable, resilient, and rigid material such as stainless steel. The handle 14 has a handgrip 16 and two arms 18 and 20 extending from one end of the handgrip 16. The handle 14 of the device can be sterilized after each surgery and then reused. The roller 22 is attached to the handle arms 18 and 20 through an attachment apparatus 25 and 27 which engages the two attachment ends 19 and 21 to openings 30 and 32 in each roller side 26 and 28 as shown hereinafter.

Figure 3:
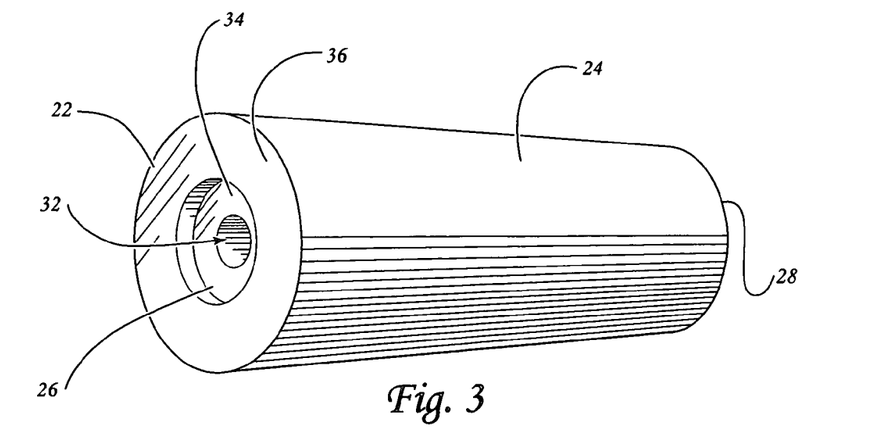
FIG. 3 is a perspective side view of a roller according to an embodiment of the present invention.

The roller 22, as shown in FIG. 3, is cylindrical in shape with a surface 24 and two sides 26 and 28 for rotatably engaging the attachment ends 19 and 21 of the arms 18 and 20. Each roller side 26 or 28 has an opening 30 or 32 through the center thereof. The roller 22 has a flexible outer surface 24 composed of a spongy material, such as foam, and is conformable to the various sizes and contours of patients' calves. The roller 22 may be composed of more than one layer, and may have an inner part 34 composed of a resilient material and an outer part 36 composed of a spongy material. The inner and outer parts 34 and 36 are cylindrical with the outer part 36 having an opening therethrough the middle, as shown. The inner part 34 is firmly engaged through the opening in the outer part 36. The inner part 34 of the roller 22 may be autoclavable and reused, or it may be thrown away after each use. The inner part 34 need not be hollow but has openings in the sides thereof of sufficient depth to firmly engage the two attachment ends 19 and 21 of the handle arms 18 and 20.

The inner part 34 of the roller 22 is made up of a rigid substance, such as plastic or stainless steel, and is rotatably attached to the attachment ends 19 and 21 of the arms 18 and 20 of the handle 14. The inner part 34 of the roller 22 is sufficiently rigid to withstand the pressure from the user's hand. The roller 22 is detachable and can be replaced for each surgery. Alternatively, the outer part 36 having the foam layer surface 24 may be replaced for each surgery and the inner part 34 may be autoclaved.

Figure 4A:
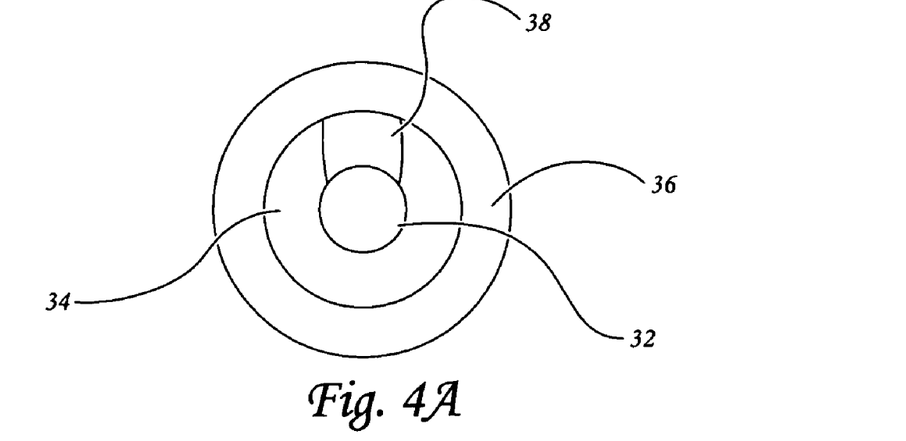
FIG. 4a is an end view of a roller according to an embodiment of the present invention.
Figure 4B:
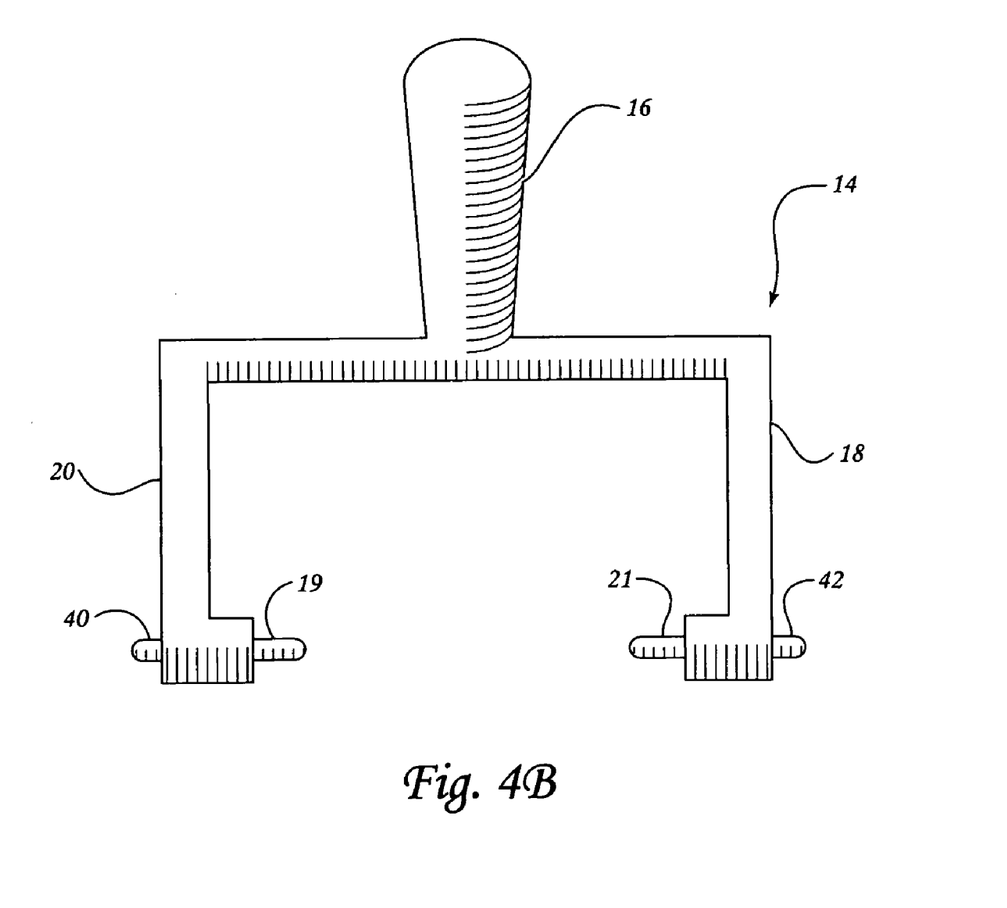

The two arms 18 and 20 are provided so that the pressure is evenly distributed on the patient's leg. The arms 18 and 20 are formed at the attachment ends 19 and 21 to rotatably engage the opposing openings 30 and 32 of the roller 22, as shown. FIGS. 4A and 4B show embodiments of the roller 22 and handle 14, which allows the attachment ends 19 and 21 to engage the roller openings 30 and 32. A slot 38 in the sides of the roller's inner part 34 permits easier engagement of the attachment ends 19 and 21 of the arms 18 and 20 therein. The attachment ends 19 and 21 may be disposed on retractable pins 40 and 42 which permit easier attachment. The retractable pins 40 and 42 should have a means for rigidly affixing them in place, such as a locking mechanism, like a snap, threaded surfaces, latch, or the like (not shown).

The spongy material on the surface 24 of the roller 22 may be taken from the group consisting of cotton, rayon, gauze, polyester, hydrophilic foam, polyvinyl acetate foam, and polyurethane foam. Any suitably absorbent and spongy material is acceptable and the invention is not seen as limited to the list provided.

Figure 5:
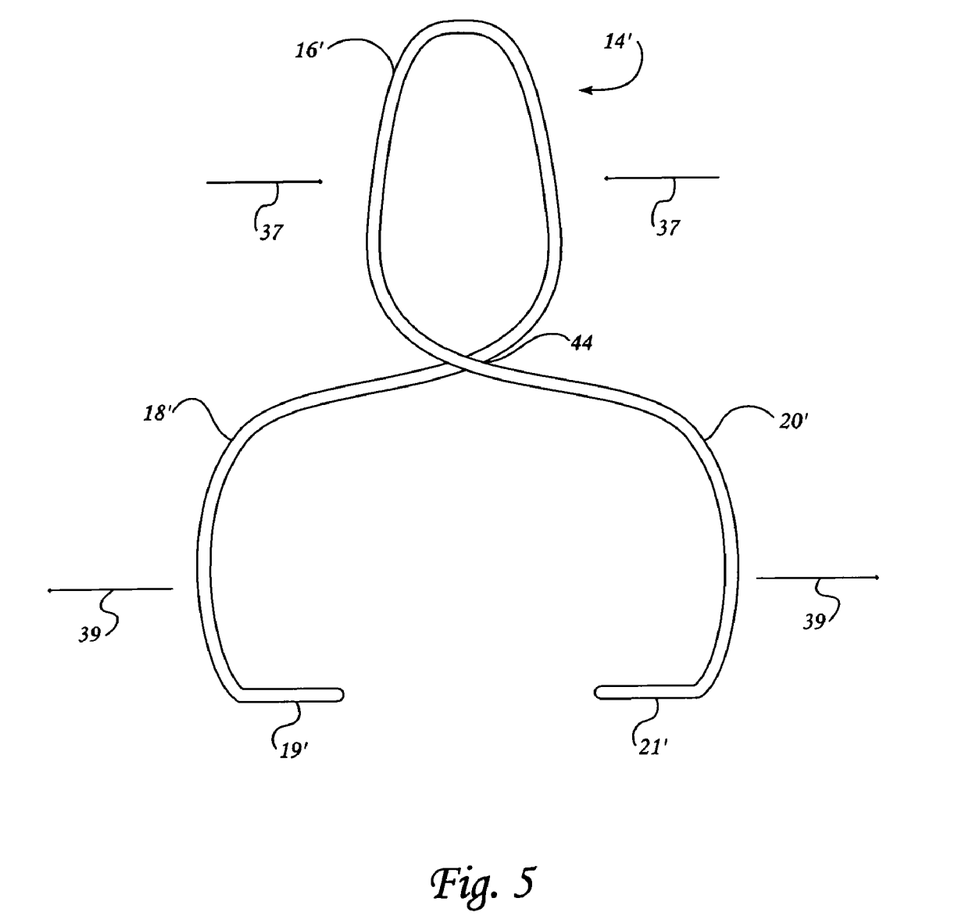
FIG. 5 is a side view of a roller handle, which may be used with the type of roller depicted in FIG. 3, of the embodiment of the present invention depicted in FIG. 1.

In another embodiment of the roller device 12' according to the present invention, the handle 14' is a bent piece of metal curved, as shown in FIG. 5, to form a handgrip 16' and cross 44 to form two arms 18' and 20' such that squeezing the handgrip 16', as shown by the arrows 37, widens the arms 18' and 20', as shown by the arrows 39. The ends 19' and 21' of the arms 18' and 20' are bent to engage the openings 30 and 32 on a roller 22. The handle 14' is autoclavable.

Figure 6:
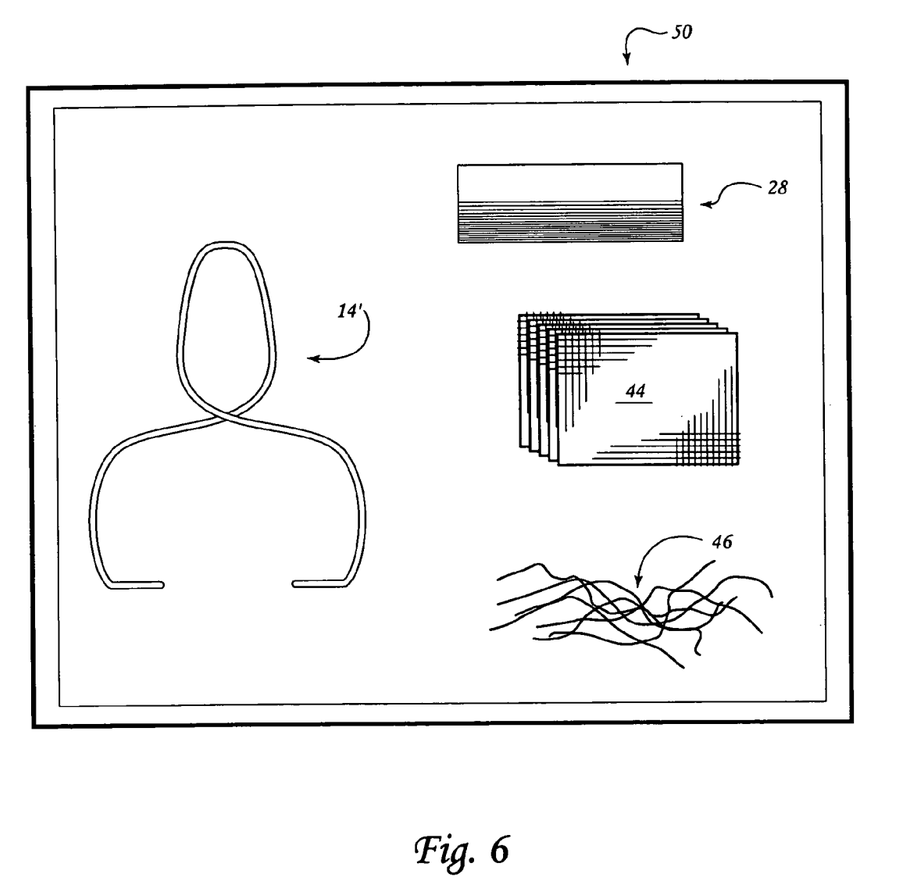
FIG. 6 is a schematic representation of a kit including an extravascular handle and roller according to an embodiment of the present invention.

The present invention may be provided in a kit 50 as shown in FIG. 6 with handle 14', roller 22, and extra gauze 44 and sutures 46. The kit 50 should be vacuum packed, or otherwise placed in a sealed package, to maintain the sterility of all components of the kit prior to surgical use. The gauze 44 included with the kit may be used to clean the subcutaneous fluid drained from the lower incision following closure of both upper 17 and lower 23 incisions on the patient's leg with depicted suture 46.

Figure 7:
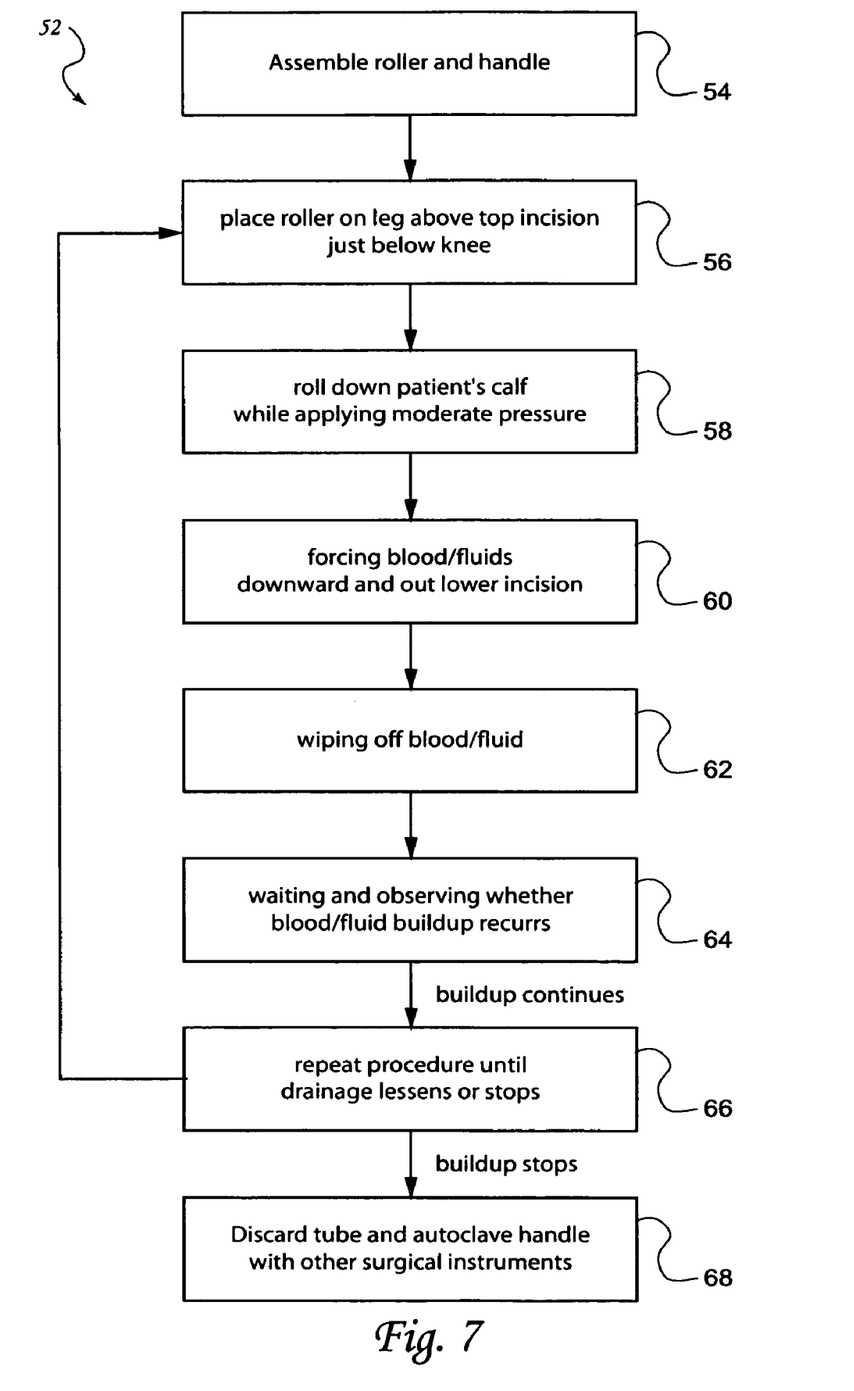
FIG. 7 is a flow chart depicting steps for using the extravascular roller according to the present invention to remove subcutaneous fluid from the site of a harvested saphenous vein.

A method of using the roller device 12 to remove blood and fluids which pool in the leg L following the removal of a saphenous vein during coronary bypass grafting procedures is also contemplated by the present invention. FIG. 7 is a flow chart 52 depicting the typical steps involved in the method contemplated by the present invention. The removal of the saphenous vein involves at least one incision, the upper incision 17, and a distal incision adjacent to the ankle, the lower incision 23.

Figure 1:
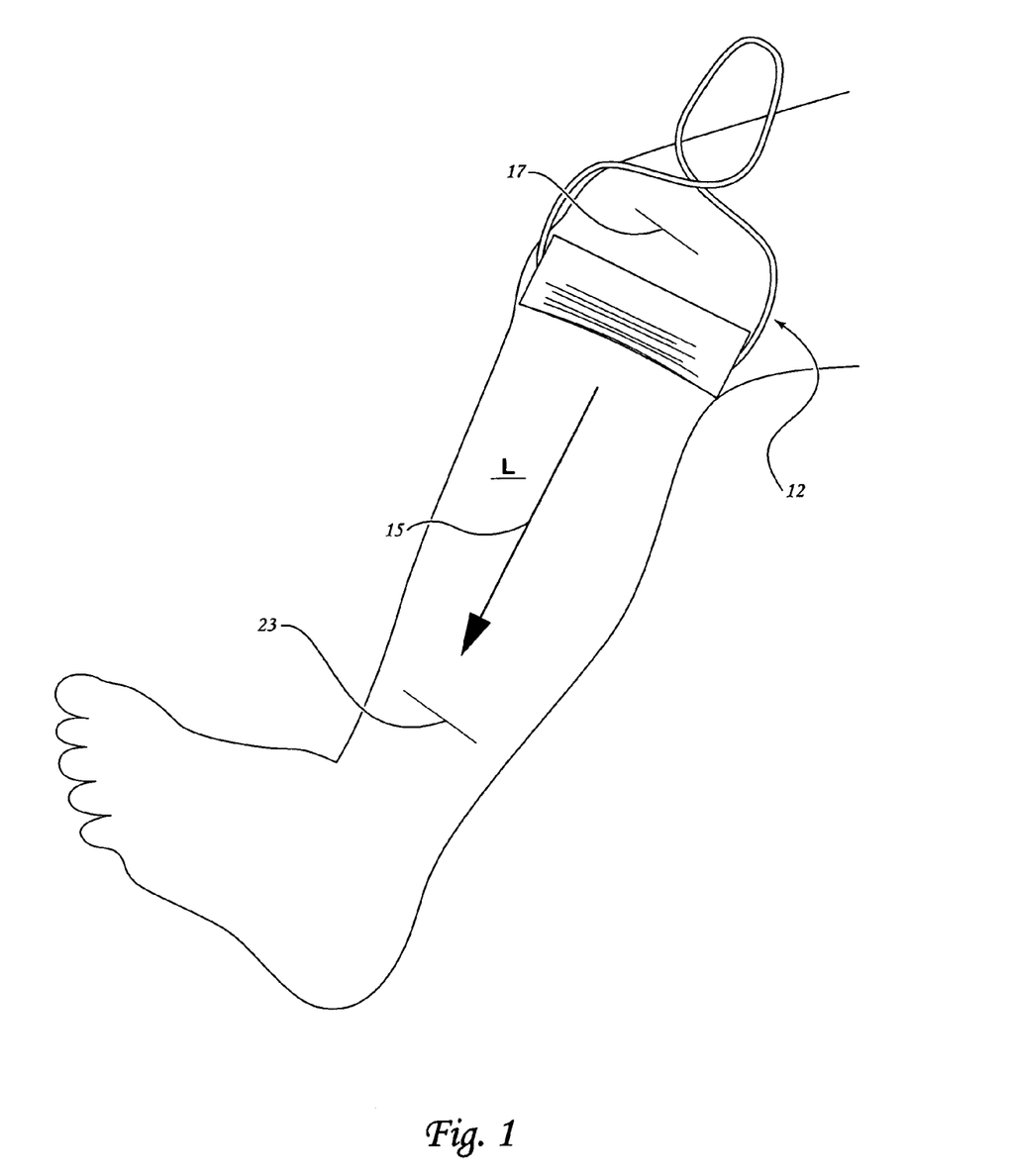
FIG. 1 is an environmental view of an extravascular roller, according to embodiment of the present invention, used on a patient's leg after the removal of a saphenous vein.

Initially, a roller device 12 or 12' according to the present invention is provided and assembled, denoted 54 in the flow chart 52. The device may be assembled from a kit 50 having a handle 14' and roller 22 according to the present invention plus gauze 44 and sutures 46. The roller is placed on the leg L above the upper incision 17, as shown in FIG. 1, just below the knee, denoted in the flow chart 52 at 56. The device is rolled down the leg L from just above the upper incision 17 and below the knee to the lower incision 23, at 58. While the surgeon rolls the device 12 down the patient's leg L, as indicated by the arrow 15, the user applies moderate pressure to the device and forces fluids downward and out of the lower incision 17, as indicated in the flow chart at 60. Gauze, or another sterilized absorbent material, is used to remove the fluid from the lower incision 62.

Afterwards, the leg L is observed for further build up of fluids 64. As further build up of fluids are found, the procedures of rolling the roller 12 down the leg L and forcing the fluid out the lower incision 23 is repeated, 66, until the observed drainage lessens significantly. When the procedure is complete, in some embodiments the roller 22 is discarded and the handle 14 or 14' is autoclaved, denoted 68, and in other embodiments the inner part 34 is also autoclaved while the outer part 36 is discarded.

It is to be understood that the present invention is not limited to the embodiments described above, but encompasses any and all embodiments within the scope of the following claims.

What is claimed is:

1. A kit containing an extravascular roller device, comprising:
   an extravascular roller device, sutures, and gauze wherein the extravascular roller device has
   a. a roller and a handle;
   b. the roller being cylindrical in shape with an external surface and two sides,
      i. each side having an opening through a center thereof,
      ii. the external surface is composed of a spongy material;
   c. the handle has a handgrip and two arms extending opposite the handgrip,
      i. wherein each arm has means for rotatably engaging an opening in each side of the roller; and
   d. the roller being rotatably engaged on the arms opposite the handgrip.

2. The kit of claim 1, wherein:
   a. the spongy material is taken from the group consisting of cotton, rayon, gauze, polyester, hydrophilic foam, polyvinyl acetate foam, polyurethane foam, and combinations thereof.

3. The kit of claim 1, wherein:
   a. the roller further comprises
      i. an inner part and an outer part;
      ii. the inner and outer parts being cylindrical;
      iii. the outer part having
         1. an external surface and being composed of a spongy material, and
         2. an opening therethrough to receive the inner part firmly therein; and
      iv. the inner part
         1. being fully engaged in the opening of the outer part prior to use, and
         2. having the side openings for rotatably engaging the arms.

4. The kit of claim 3, wherein:
   a. the spongy material is taken from the group consisting of cotton, rayon, gauze, polyester, hydrophilic foam, polyvinyl acetate foam, and polyurethane foam.

5. The kit of claim 1, wherein:
   a. the handle comprises
      i. a bent piece of metal or other resilient material curved in the middle to form a handgrip, and
      ii. crossed opposite the handgrip to form two opposing arms such that squeezing the handgrip widens the arms; and
      iii. the arms having means for rotatably engaging the openings opposite the handgrip.

6. A method for removing built up fluid from a leg following the removal of a saphenous vein, which removal involves at least one upper incision below the knee and a lower incisions adjacent the ankle, the method comprising the steps of:
   a. providing an extravascular roller device having
      i. a roller and a handle;
      ii. the roller being cylindrical in shape with an "external surface" and two sides,
         1. each side having an opening through a center thereof,
         2. the "external surface" is composed of a spongy material;
      iii. the handle has a handgrip and two arms extending opposite the handgrip,
         1. wherein each arm has means for rotatably engaging an opening in each side of the roller; and
      iv. the roller being rotatably engaged on the arms opposite the handgrip;
   b. rolling the device down the leg from just above the upper incision and below the knee to the lower incision; and
   c. forcing fluids downward and out of the lower incision.

7. The method of claim 6 further comprising the steps of:
   a. placing the roller on the leg above the top incision just below the knee;
   b. applying moderate pressure to the device; and
   c. removing fluid from the lower incision.

8. The method of claim 6, further comprising the steps of:
   a. observing leg for further build up of fluids;
   b. repeating the steps of
      i. rolling the device down the leg, and
      ii. forcing fluids downward and out of the lower incision until drainage lessens or stops; and
   c. finding build up of fluids.

9. The method of claim 8, further comprising the steps of:
   a. observing drainage lessening;
   b. discarding the tube; and
   c. autoclaving the handle.

10. The method of claim 6, further comprising the steps of:
    a. assembling roller device from kit containing handle and roller with spongy surface, and gauzes.

11. The method of claim 6, wherein:
    a. the roller further comprises
       i. an inner part and an outer part;
       ii. the inner and outer parts being cylindrical;
       iii. the outer part having
          1. an external surface and being composed of a spongy material, and
          2. an opening therethrough to receive the inner part firmly therein; and
       iv. the inner part
          1. being fully engaged in the opening of the outer part prior to use, and v. having the side openings for rotatably engaging the arms.

12. The method of claim 6, wherein:

a. the handle comprises
   i. a bent piece of metal or other resilient material curved in the middle to form a handgrip, and
   ii. crossed opposite the handgrip to form two opposing arms such that squeezing the handgrip widens the arms; and
   iii. the arms having means for rotatably engaging the openings opposite the handgrip.

* * * * *